United States Patent [19]

Röchling et al.

[11] Patent Number: 5,200,401
[45] Date of Patent: Apr. 6, 1993

[54] WATER-DISPERSIBLE GRANULES OF NEOPHANS AND AZANEOPHANS FOR USE IN PLANT PROTECTION

[75] Inventors: Hans Röchling, Bad Soden am Taunus; Joachim Baumgärtner, Frankfurt am Main, both of Fed. Rep. of Germany

[73] Assignee: Hoechst Aktiengesellschaft, Frankfurt am Main, Fed. Rep. of Germany

[21] Appl. No.: 656,291

[22] Filed: Feb. 15, 1991

[30] Foreign Application Priority Data

Feb. 17, 1990 [DE] Fed. Rep. of Germany ....... 4005154

[51] Int. Cl.⁵ .................... A01N 55/00; A61K 31/695
[52] U.S. Cl. ...................... 514/63; 514/937; 514/941
[58] Field of Search .................. 514/63, 941, 937

[56] References Cited

U.S. PATENT DOCUMENTS

| | | | |
|---|---|---|---|
| 2,457,724 | 4/1951 | Sundholm | 514/442 |
| 4,511,395 | 4/1985 | Misselbrook | 71/124 |
| 4,775,664 | 10/1988 | Schubert et al. | 514/63 |
| 4,804,653 | 2/1989 | Strunk et al. | 514/63 |
| 4,864,027 | 9/1989 | Shubert et al. | 546/14 |
| 4,966,902 | 10/1990 | Schubert et al. | 514/63 |

FOREIGN PATENT DOCUMENTS

| | | |
|---|---|---|
| 202893 | 11/1986 | European Pat. Off. . |
| 0336199 | 3/1989 | European Pat. Off. . |
| 3604781 | 8/1987 | Fed. Rep. of Germany . |

OTHER PUBLICATIONS

The Merck Index, 10th Edition, Merck & Co, Rathway, NJ 1983, p. 1273.
Chemical Abstracts, vol. 109, No. 1: Jul. 4, 1988.

*Primary Examiner*—Allen J. Robinson
*Assistant Examiner*—B. Bembenick
*Attorney, Agent, or Firm*—Curtis, Morris & Safford

[57] ABSTRACT

Water-dispersible granules of compounds of the formula I

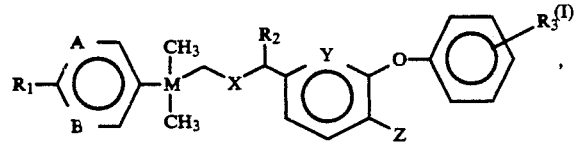

in which
A and B independently of one another are CH, $CR_4$ and N,
X is $CH_2$, O, or S,
Y is CH or N,
Z is H or F,
$R_1$ and $R_4$ independently of one another are H, halogen, ($C_1$–$C_3$)-alkyl, ($C_1$–$C_3$)-halogenoalkyl, ($C_1$–$C_3$)-alkoxy, ($C_1$–$C_3$)-halogenoalkoxy, ($C_1$–$C_4$)-alkylthio, or ($C_1$–$C_4$)-halogenoalkylthio, or $R_1$ and $R_4$ together are —$CH_2$—O—$CH_2$—;
$R_2$ is H, ($C_1$–$C_3$)-alkyl, ethinyl, vinyl, halogen, cyano,
$R_3$ is H, halogen, ($C_1$–$C_4$)-alkyl, ($C_1$–$C_3$)-alkoxy and
M is C or Si,
which contain, in addition to finely divided highly absorptive silica and suitable wetting and dispersing agents, an aluminum silicate or magnesium aluminum silicate and a mono-, di- or trisaccharide, have a high spontaneous dispersibility, a very low wet-screening residue and very good storage-stability properties.

7 Claims, No Drawings

WATER-DISPERSIBLE GRANULES OF NEOPHANS AND AZANEOPHANS FOR USE IN PLANT PROTECTION

DESCRIPTION

The present invention relates to water-dispersible granules of compounds of the formula I

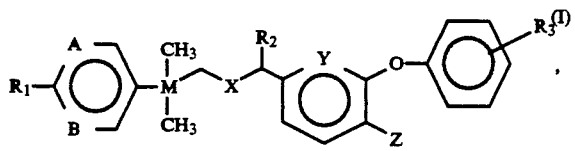

in which

A and B independently of one another are CH, $CR_4$ and N,

X is $CH_2$, O, or S,

Y is CH or N,

Z is H or F, $R_1$ and $R_4$ independently of one another are H, halogen, ($C_1$–$C_3$)-alkyl, ($C_1$–$C_3$)-halogenoalkyl, ($C_1$–$C_3$)-alkoxy, ($C_1$–$C_3$)-halogenoalkoxy, ($C_1$–$C_4$)-alkylthio, or ($C_1$–$C_4$)-halogenalkylthio, or $R_1$ and $R_4$ together are —$CH_2$—O—$CH_2$-;

$R_2$ is H, ($C_1$–$C_3$)-alkyl, ethinyl, vinyl, halogen, cyano, $R_3$ is H, halogen, ($C_1$–$C_4$)-alkyl, ($C_1$–$C_3$)-alkoxy and M is C or Si, which contain, in addition to finely divided highly absorptive silica and suitable wetting and dispersing agents, an aluminum silicate or magnesium aluminum silicate and a mono-, di- or trisaccharide.

Alkyl represents a straight-chain or branched alkyl radical.

Preferably, A and B are CH or N, X is $CH_2$, $R_1$ is ($C_1$–$C_3$)-alkoxy, $R_2$ is H, $R_3$ is H or F and M is Si.

Particularly preferred among the compounds of the formula

I is that in which M is Si, $R_1$ is ethoxy, A and B are CH, X is $CH_2$, $R_2$ is H, Y is CH, Z is F and $R_3$ is H (Ia).

Active substances from the group of the neophans and the azaneophans (I) are suitable for controlling animal pests, in particular insects, arachnids and nematodes, which occur in agriculture, in forests, in the protection of stored goods and materials and in the hygiene field, while having good compatibility with plants and favorable toxicity towards warm-blooded species. They are effective against normally sensitive and resistant species and against all or individual stages of development (EP-A 0,224,024, EP-A 0,249,015, EP-A 0,288,810). These documents also describe the customary formulation types for insecticides or acaricides.

In addition to a broad insecticidal activity, neophans and aza neophans of the formula I have an unusually favorable toxicity to warm-blooded species and a very low toxicity to fish and birds. It was intended to assist these positive properties of the active substance by a suitable formulation. A liquid formulation in the form of an aqueous emulsion (EW) first seems to be expedient, since the compounds I are present as oily substances which are very sparingly soluble in water and have a high boiling point.

However, some countries require solid formulations in the form of wettable powders, in particular when used in fruit and tea growing. Wettable powders, however, produce dust when manufactured and used; there is therefore a risk of dust explosion and of contamination of the user.

An ecologically acceptable alternative to wettable powder formulations are water-dispersible granules, since the latter are free-flowing, low in dust, can be measured out with ease and are free from solvents. They can be packaged without problems in polyethylene containers, laminated film bags with cardboard boxes or in cardboard drums, which are readily disposable.

A large number of processes is available for preparing dispersible granules (cf. H. B. Ries "Granuliertechnik und Granuliergeräte" [Granulation Technology and Granulation Apparatus]in Aufbereitungstechnik Nr. 3, 1970, p. 147 and M. Rosch und R. Probst in Verfahrenstechnik 9 (1975), p. 59 to 64). These publications describe, in particular, the preparation of water-dispersible granules using the fluidized-bed process, see U.S. Pat. No. 3,920,442, GB-A 1,401,304, EP-A 242,845, German Patent Applications P 3,909,455.3 and P 3,926,800.4, and also M. Rosch and R. Probst in Verfahrenstechnik 9 (1975), pp. 59-62. However, the processes and formulations described therein cannot be used advantageously in the case of the neophans and azaneophans (I). This is because the active substances of the formula I are oily liquids which must therefore be adsorbed on a carrier in the form of a powder before they are granulated. Suitable adsorbents which are employed are highly adsorptive precipitated silicas. Subsequent granulation by spraying the adsorbate with a solution of wetting and dispersing agents in a fluidized bed gives granules which can only be dispersed in water with difficulty, have high wet-screening residues and therefore present problems when used in practice (see Preparation Example 1).

It was therefore an object to develop water-dispersible granules of neophans and azaneophans (I) which have good storage stability while additionally having a high spontaneous dispersibility and as low a wet-screening residue as possible.

It has been found that a marked improvement in the spontaneous dispersibility and a considerable reduction of the wet-screening residues can be achieved by adding mono-, di- or trisaccharides in a ratio by weight of highly-adsorptive silica: mono-, di- or trisaccharide of 1:1.8 to 1:3 (Preparation Example 2). In addition, the stability of the individual granules is improved by adding mono-, di- or trisaccharides.

However, the granules according to Example 2 do not yet have sufficient storage stability: a high wet residue is observed after 14 days' storage at 54° C.

It has now been found in a surprising manner that water-dispersible granules which have very good technical properties in use and good storage stability can be obtained when the adsorbate is mixed with an aluminum silicate or a magnesium aluminum silicate, followed by granulation with a spray solution which contains a mono-, di- or trisaccharide in the amount indicated as well as suitable wetting agents and dispersants (Preparation Examples 4 to 7).

Examples of aluminum silicates which can be employed are: finely ground kaolines and clays, ®Perlite (Lehmann & Voss & Co.), calcined aluminum silicate such as ®Satintone (manufactured by Engelhard), and the following are examples of magnesium aluminum silicates which can be used: Attapulgus Clay products such as ®Attaclay, ®Attacote, ®Attasorb, ®Attagel (manufactured by Engelhard) and also finely ground Fuller's earths, bentonites and montmorillonites. The use of ®Attasorb, ®Satintone and Kaolin 1777 (Ziegler and Co., Wunsiedel) is particularly favorable.

The following may be mentioned as examples of mono-, di- or trisaccharides: glucose, fructose, maltose, cellobiose, lactose, sucrose, raffinose; but also polysaccharides, for example maltodextrin, can be employed according to the invention. The use of sucrose is particularly advantageous.

Examples of suitable wetting agents and dispersants are anionic or cationic, amphoteric and non-ionic surface-active substances, in particular customary anionic dispersants, such as the Na salt of the sulfonic acid formed from m-cresol+formaldehyde+Na sulfite (dispersant 1494 ®), sodium oleylmethyltauride (®Arkopon T), sodium methoxyligninsulfonate (®Vanisperse CB), sodium ligninsulfonate (®Borresperse 3A), sodium methylnaphthalene sulfonate (®Supragil MNS 90), tricyclic nonylphenol novolak (18 EO) sulfosuccinic acid monoester, sodium salt (dispersant 1728 ®, 18EO=ethoxylated with 18 mol of ethylene oxide), the sodium salt of isodecylsulfosuccinic acid monoester (wetting agent IS ®), the sodium salt of dinaphthylmethanedisulfonic acid (®Dispersogen A, ®Tamol NNO), the sodium salt of a sulfonic acid formed from cresol+formaldehyde+Na sulfite+oxynaphthalenesulfonic acid (dispersant) SS ®), the sodium salt of dibutylnaphthalenesulfonic acid (®Leonil DB, ®Geropon NK), sodium polycarboxylate (®Sopropon T36), potassium polycarboxylate (®Dispersant DG), sodium phenylsulfonate (®Dispersant GN), sodium alkyl naphthalene sulfonate (®Supragil WP), condensed sodium naphthalene sulfonate (®Supragil NS 90), the Na or K salt of a carboxylated copolymer in combination with an anionic dispersant (®Geropon SC 211 or 213, manufactured by Rhône Poulenc), and also calcium lignisulfonates or sodium lignisulfonates of various origins; the Na salt of a copolymer of maleic acid and an olefine (®Sokalan CP brands, manufactured by BASF), the sodium salt of a phenol sulfonic acid condensation product having anionic character (®Tamol PP, manufactured by BASF), sodium/naphthalenesulfonate/formaldehyde condensation products (®Morwet D-425, manufactured by DeSoto Inc., ®Tamol N brands, manufactured by BASF), phosphorylated ethylene oxide/propylene oxide block polymers (for example Hoe S 3618, manufactured by Hoechst AG; Alkaphos MD types, manufactured by Alkaril), ethoxylated and phosphorylated styryl-substituted phenols (for example Hoe S 3775, manufactured by Hoechst AG; ®Soprophor FL, manufactured by Rhône Poulenc) and sodium lauryl ether phosphate (®Forlanit P, manufactured by Henkel). The use of sodium polycarboxylate (®Sopropon T36), sodium methylnaphthalene sulfonate (®Supragil MNS 90), the sodium salt of dinaphthylmethane disulfonic acid (®Dispersogen A, ®Tamol NNO), sodium oleylmethyltauride (®Arkopon T), sodium isopropylnaphthalenesulfonate (®Supragil WP) and sodium dibutylnaphthalenesulfonate (®Leonil DB) is particularly favorable.

Adsorbents which can be employed are the various finely divided, highly adsorptive silicas which are obtained by precipitation: for example ®Sipernat and ®Wessalon types (manufactured by Degussa); or ®Sipernat 50 S is particularly suitable.

The granules can furthermore contain defoamers such as trialkylphosphates, silicone defoamers, for example ®Silcolapse 5008, manufactured by ICI, ®Silicon-Antischaumemulsion SE2, manufactured by Wacker Chemie, or fluorosurfactants, for example ®Fluowet PP, manufactured by Hoechst AG.

The finished formulation can contain 0.5 to 60% by weight, in particular 10 to 40% by weight, of active substances of the formula I (Ia).

The amount of precipitated silica which is used as adsorbent depends on the particular content of the compound of the formula I and is 30 to 110% by weight, preferably 50 to 80% by weight, of the amount of active substance.

The amount of aluminum silicate or magnesium aluminum silicate is 0.5 to 80% by weight of the formulation according to the invention, preferably 5 to 60% by weight.

The mono-, di- or trisaccharide content in the finished formulations can be 5 to 80% by weight, preferably 20 to 60% by weight; in particular, it depends on the content of highly adsorptive silica and is in a ratio by weight of silica : mono-, di- or trisaccharide=1:1.8 to 1:3.

The amount of wetting agents and dispersants is 3 to 30% by weight, preferably 5 to 20% by weight, of the formulation.

The water-dispersible granules according to the invention can also contain mixtures of various silicas, various silicates or various saccharides. It is preferred to employ mixtures of various representatives as the wetting agent and dispersant (see Exemplary Embodiments).

All formulation auxiliaries mentioned are substances which are sufficiently known to those skilled in the art and which are described in the literature. For example: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; Marschen, "Solvents Guide", 2nd Ed., Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte", [Surface-active Ethylene Oxide Adducts], Wiss. Verlagsgesell., Stuttgart 1976; Winnacker-Küchler, "Chemische Technologie", [Chemical Technology], Volume 7, C. Hauser Verlag Munich, 4th edition 1986.

To prepare the water-dispersible granules, finely divided silica is first mixed with aluminum silicate or magnesium aluminum silicate, active substance of the formula I is subsequently added, and the mixture is treated in a mixer until homogeneous. It is also possible to first absorb the active substance to silica and subsequently mix the adsorbate with aluminum silicate or magnesium aluminum silicate. The adsorbate obtained is granulated in a fluidized bed by spraying with an aqueous solution of mono-, di- or trisaccharide and wetting agents and dispersants.

PREPARATION EXAMPLES

General information for assessment and preparation

The spontaneous dispersibility of the granule formulation is assessed using a key from 1 to 4. For this purpose, 1 g of the granules is first placed in a 1 l measuring cylinder filled with standardized water (30° C., 342 ppm hardness). After 1 minute, the measuring cylinder is slowly rotated by 180° C. and returned into the starting position. This procedure is repeated three times. The following key is used in the assessment:

Key

1 All granule particles are dispersed.
  If undispersed granules remain, the cylinder is shaken another three times as described 2 minutes after the test has been set up and assessed as follows:
2 The granules are now completely dispersed.
3 Some granules are not dispersed.
4 Most of the granules are not dispersed.

The suspendibility is indicated as the amount of preparation (% by weight) which is located in the upper nine tenths part by volume of the suspension after a sedimentation time of 30 minutes has elapsed (see CIPAC-Handbook Vol. 1 (1970), p. 861).

The wet-screening residue denotes the amount of substance which remains on a 250 μm or 71 μm screen after 10 minutes washing with a defined amount of water. A description of the method can be found in "Richtlinien für die amtliche Prüfung von Pflanzenschutzmitteln" [Guidelines for the Official Testing of Plant Protection Agents], Biol. Bundesanstalt Braunschweig (1988).

A Lödige mixer is used for preparing the adsorbates: Gebr. Lödige, Maschinenbau GmbH, D-479 Paderborn. A laboratory fluidized-bed granulator Büchi 170 (Büchi Laboratoriumstechnik GmbH, P.O. Box 11 54, 7332 Eislingen/Fils) is used for granulating small amounts. An Aeromatic fluidized-bed laboratory apparatus size 1, manufactured by Aeromatic AG, CH-4416 Bubendorf/Switzerland, is used for batches up to 400 g of product. Larger batches up to 15 kg of product are carried out on a fluidized bed manufactured by Glatt (GPCG 5).

EXAMPLE 1

Granules without mono-, di- or trisaccharide and without aluminum silicate or magnesium aluminum silicate.

| | |
|---|---|
| 21.5% by weight of | a compound of the formula I (Ia) are adsorbed on |
| 55.5% by weight of | finely divided, highly adsorptive silica ( ® Sipernat 50S) by intensive mixing in a Lödige mixer. The resulting adsorbate is granulated in a laboratory fluidized-bed granulator Büchi 710 by spraying with a solution of |
| 12.0% by weight of | potassium salt of a carboxylated copolymer in combination with anionic dispersants ( ® Geropon SC 213), |
| 8.0% by weight of | sodium polycarboxylate ( ® Sopropon T36) and |
| 55.0% by weight of | water. |

| | |
|---|---|
| Residual moisture: | 3.0% |
| Spontaneous dispersibility: | 3–4 |
| Suspendibility: | 53% |
| Wet-screening residue, 250 μm screen: | 1.2% 71 μm screen: 19.7% |

EXAMPLE 2

Granules without aluminum silicate or magnesium aluminum silicate

| | |
|---|---|
| 21.7% by weight of | a compound of the formula I (Ia) or adsorbed on |
| 22.3% | by weight of ® Sipernat 50S by intensive mixing in a Lödige mixer. The resulting adsorbate is granulated in a laboratory fluidized-bed granulator Büchi 710 by spraying with a solution of |
| 6.0% by weight of | ® Geropon SC 213, |
| 4.0% by weight of | ® Sopropon T36 and |
| 45.0% by weight of | sucrose in |
| 56.0% by weight of | water |

Water-dispersible granules of a particle size of 0.5–1.8 mm are obtained in a yield of 87%

| | |
|---|---|
| Residual moisture: | 1.0% |
| Spontaneous dispersibility: | 1 |
| Suspendibility: | 94% |
| Wet-screening residue, 250 μm screen: | trace 71 μm screen: 0.1% |

The technical properties in use deteriorate drastically after storage for 14 days at 54° C. under pressure (25 g/cm$^2$) (CIPAC Handbook, Vol. /1 (1970), p. 951).

| | |
|---|---|
| Spontaneous dispersibility: | 3–4 |
| Suspendibility: | 70.4% |
| Wet-screening residue, 250 μm screen: | trace 71 μm screen: 19.5% |

EXAMPLE 3

| | |
|---|---|
| 21.7% by weight of | a compound of the formula I (Ia) or adsorbed on a mixture of |
| 16.0% by weight of | ® Sipernat 50S |
| 10.8% by weight of | calcined aluminum silicate ( ® Satintone No. 5) by intensive mixing in a Lödige mixer. The resulting adsorbate is granulated in a laboratory fluidized-bed granulator Büchi 710 by spraying with a solution of |
| 6.0% by weight of: | ® Geropon Sc 213 |
| 4.0% by weight of: | ® Sopropon T36 |
| 0.5% by weight of: | ethoxylated and phosphorylated styryl-substituted phenol (HOE S 3775) and |
| 40.0% by weight of: | sucrose in |
| 55.0% by weight of: | water. |

Water-dispersible granules having a particle size of 0.3–1.6 mm are obtained in a yield of 84%.

| | |
|---|---|
| Residual moisture: | 1.0% |
| Spontaneous dispersibility: | 1 |
| Suspendibility: | 94% |
| Wet-screening residue, 250 μm screen: | trace 71 μm screen: 0.15% |

The technical properties in use of the granules after storage for 14 days at 54° C. under pressure (25 g/cm²) are fully satisfactory:

| Spontaneous dispersibility: | 2 |
| --- | --- |
| Suspendibility: | 83.6% |
| Wet-screening residue, | |
| 250 μm screen: | 0 71 μm screen: 0.5% |

EXAMPLE 4

| 21.7% by weight of | a compound of the formula I (Ia) are adsorbed on a mixture of |
| --- | --- |
| 15.0% by weight of | ® Sipernat 50S |
| 11.8% by weight of | Magnesium aluminum silicate (® Attasorb RVM) by intensive mixing in a Lödige mixer. The resulting adsorbate is granulated in a laboratory fluidized-bed granulator Büchi 710 by spraying with a solution of |
| 6.0% by weight of | ® Geropon SC 213 |
| 4.0% by weight of | ® Sopropon T36 |
| 0.8% by weight of | sodium lauryl ether phosphate (® Forlanit P) and |
| 39.7% by weight of | sucrose in |
| 57.0% by weight of | water. |

Water-dispersible granules having a particle size of 0.25–1.5 mm are obtained in a yield of 86%.

| Residual moisture: | 1.0% |
| --- | --- |
| Spontaneous dispersibility: | 1 |
| Suspendibility: | 95% |
| Wet-screening residue, | |
| 250 μm screen: | 0 71 μm screen: trace |

The technical properties in use of the granules after storage for 14 days at 54° C. under pressure (25 g/cm²) are fully satisfactory:

| Spontaneous dispersibility: | 1 |
| --- | --- |
| Suspendibility: | 88.4% |
| Wet-screening residue, | |
| 250 μm screen: | trace 71 μm screen: 0.2% |

EXAMPLE 5

Preparation as described for Examples 3 and 4.

| 21.7% by weight of | a compound of the formula I |
| --- | --- |
| 15.0% by weight of | ® Sipernat 50S |
| 11.8% by weight of | ® Attasorb RVM |
| 0.5% by weight of | ® Forlanit P |
| 10.0% by weight of | the sodium salt of dinaphthylmethane disulfonic acid (® Tamol NNO) |
| 5.0% by weight of | dibutylnaphthalenesulfonic acid (® Leonil DB) |
| 2.0% by weight of | sodium oleoylmethyltauride (® Arkopon T) |
| 32.0% by weight of | sucrose |
| 2.0% by weight of | residual moisture |

| Spontaneous dispersibility: | 1 |
| --- | --- |
| Suspendibility: | 88% |
| Wet-screening residue, | |
| 250 μm screen: | trace 71 μm screen: 0.19% |

After storage for 14 days at 54° C. and 25 g/cm² pressure:

| Spontaneous dispersibility: | 1 |
| --- | --- |
| Suspendibility: | 81% |
| Wet-screening residue, | |
| 250 μm screen: | trace 71 μm screen: 0.28% |

EXAMPLE 6

Preparation as described in Examples 3 and 4.

| 21.7% by weight of | a compound of the formula I |
| --- | --- |
| 15.0% by weight of | ® Sipernat 50S |
| 11.8% by weight of | ® Attasorb RVM |
| 5.0% by weight of | ® Leonil DB |
| 2.0% by weight of: | Arkopon T |
| 10.0% by weight of | sodium naphthalenesulfonate/formaldehyde condensation product (® Morwet D-425) |
| 32.0% by weight of | sucrose |
| 2.0% by weight of | residual moisture |

| Spontaneous dispersibility: | 1 |
| --- | --- |
| Suspendibility: | 93% |
| Wet-screening residue, | |
| 250 μm screen: | 0 71 μm screen: 0.31% |

After storage for 14 days at 54° C. and 25 g/cm² pressures:

| Spontaneous dispersibility: | 1 |
| --- | --- |
| Suspendibility: | 84% |
| Wet-screening residue, | |
| 250 μm screen: | 0 71 μm screen: 0.42% |

EXAMPLE 7

Preparation as described for Examples 3 and 4.

21.5% by weight of a compound of the formula I
15.0% by weight of ® Sipernat 50S
11.0% by weight of ® Attasorb RVM
2.0% by weight of ® Arkopon T
3.0% by weight of ® Leonil DB
3.0% by weight of ® Sopropon T36
2.0% by weight of ® Tamol NNO
40.5% by weight of sucrose
2.0% by weight of residual moisture

| Spontaneous dispersibility: | 1 |
| --- | --- |
| Suspendibility: | 94% |
| Wet-screening residue, | |
| 250 μm screen: | trace 71 μm screen: 0.2% |

After storage for 14 days at 54° C. and 25 g/cm² pressures:

| Spontaneous dispersibility: | 1 |
| --- | --- |
| Suspendibility: | 90% |
| Wet-screening residue, | |
| 250 μm screen: | trace 71 μm screen: 0.37% |

We claim:
1. Water-dispersible granules which contain 0.5 to 60% by weight of a compound of the formula I

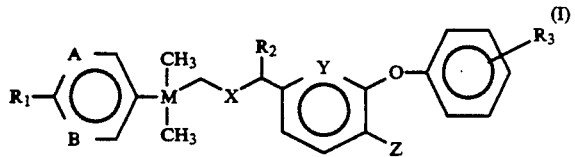

in which

A and B independently of one another are CH, CR$_4$ and N,

X is CH$_2$, O, or S,

Y is CH or N,

Z is H or F,

R$_1$ and R$_4$ independently of one another are H, halogen, (C$_1$–C$_3$)-alkyl, (C$_1$–C$_3$)-halogenoalkyl, (C$_1$–C$_3$)alkoxy, (C$_1$–C$_3$)-halogenoalkoxy, (C$_1$–C$_4$)-alkylthio, or (C$_1$–C$_4$)-halogenoalkylthio, or R$_1$ and R$_4$ together are —CH$_2$—O—CH$_2$—;

R$_2$ is H, (C$_1$–C$_3$)-alkyl, ethinyl, vinyl, halogen, cyano,

R$_3$ is H, halogen, (C$_1$–C$_4$)-alkyl, (C$_1$–C$_3$)-alkoxy and

M is Si, which contain, in addition to finely divided highly absorptive silica in the amount of 30 to 110% by weight relative to compound I, and suitable wetting and dispersing agents, an aluminum silicate or magnesium aluminum silicate and a mono-, di- or trisaccharide, wherein the ratio by weight of silica to mono-, di- or trisaccharide is 1:1.8 to 1:3.

2. The water-dispersible granules as claimed in claim 1, in which, in formula I, A and B are CH or N, X is CH$_2$, R$_1$ is (C$_1$–C$_3$)-alkoxy, R$_2$ is H, R$_3$ is H or F and M is Si.

3. The water-dispersible granules as claimed in claim 1, in which, in formula I, M is Si, R$_1$ is ethoxy, A and B are CH, X is CH$_2$, R$_2$ is H, Y is CH, Z is F and R$_3$ is H.

4. The water-dispersible granules as claimed in claim 1, which contain 0.5–80% by weight of an aluminum silicate or magnesium aluminum silicate, 5–80% by weight of mono-, di- or trisaccharide and 3–30% by weight of wetting agents and dispersants.

5. The water-dispersible granules as claimed in claim 1, which contain 5–60% by weight of an aluminum silicate or magnesium aluminum silicate, 20–60% by weight of mono-, di- or trisaccharide and 5–20% by weight of wetting agents and dispersants.

6. The water-dispersible granules as claimed in claim 1, which contain sucrose as the disaccharide.

7. A method of controlling harmful insects or acarids, which comprises applying an effective amount of water-dispersible granules as claimed in claim 1 to the plants, areas or substrates infested with these harmful insects or acarids.

* * * * *